(12) United States Patent
Polaschegg

(10) Patent No.: US 6,280,632 B1
(45) Date of Patent: Aug. 28, 2001

(54) DEVICE AND METHOD FOR PREPARATION OF SUBSTITUTION SOLUTION

(75) Inventor: Hans-Dietrich Polaschegg, Köstenberg (AU)

(73) Assignee: Gambro Lundia AB (SE)

( * ) Notice: Subject to any disclaimer, the term of this patent is extended or adjusted under 35 U.S.C. 154(b) by 0 days.

(21) Appl. No.: 09/341,335

(22) PCT Filed: Jan. 7, 1998

(86) PCT No.: PCT/SE98/00005

§ 371 Date: Jul. 8, 1999

§ 102(e) Date: Jul. 8, 1999

(87) PCT Pub. No.: WO98/30258

PCT Pub. Date: Jul. 16, 1998

(30) Foreign Application Priority Data

Jan. 9, 1997 (DE) .............................................. 197 00 466

(51) Int. Cl.[7] .......................... B01D 61/32; B01D 61/28; B01D 65/10
(52) U.S. Cl. .......................... 210/739; 210/85; 210/87; 210/90; 210/96.2; 210/97; 210/103; 210/137; 210/143; 210/321.69; 210/321.72; 210/410; 210/646; 73/40
(58) Field of Search .............................. 210/637, 644, 210/645, 646, 85, 87, 90, 96.2, 97, 103, 106, 410, 136, 137, 143, 321.69, 321.72, 739, 321.75, 741, 433.1, 434; 73/38, 40; 604/4.01

(56) References Cited

U.S. PATENT DOCUMENTS

| 4,209,391 | 6/1980 | Lipps et al. | 210/188 |
|---|---|---|---|
| 4,702,829 | * 10/1987 | Polaschegg et al. | 210/195.2 |
| 4,708,802 | 11/1987 | Rath et al. | 210/641 |
| 4,834,888 | 5/1989 | Polaschegg | 210/646 |
| 5,476,592 | 12/1995 | Simard | 210/651 |
| 5,660,722 | * 8/1997 | Nederlof | 210/90 |

(List continued on next page.)

FOREIGN PATENT DOCUMENTS

| 34 48 262 C2 | 6/1986 | (DE) . |
|---|---|---|
| 42 40 681 C2 | 6/1994 | (DE) . |
| 0 165 519 B1 | 6/1990 | (EP) . |

(List continued on next page.)

OTHER PUBLICATIONS

Hans–Dietrich Polaschegg and Nathan W. Levin, "Hemodialysis Machines and Monitors," Replacement Of Renal Function By Dialysis, Fourth Edition, C. Jacobs, C.M. Kfellstrand, K. M. Koch and J.F. Winchester, eds., Kluwer Academic Publishers, Dordrecht, The Netherlands (1996), pp. 334–379.

Primary Examiner—John Kim
(74) Attorney, Agent, or Firm—Lerner, David, Littenberg, Krumholz & Mentlik, LLP

(57) ABSTRACT

Apparatus and methods for providing sterile substitution solutions from a dialysis fluid used in connection with the treatment of a patient's blood in an extracorporeal circuit are disclosed. The apparatus includes pumps or valves for comparing the flow of fresh dialysis fluid prior to treatment and after treatment of a patient's blood and a throttle which divides the fresh dialysis circuit into a positive pressure portion and a negative pressure portion, a sterile filter including a membrane disposed in the positive pressure portion of the dialysis circuit, and a valve for controlling the pressure in the positive pressure portion to pass a predetermined amount of the fresh dialysis fluid through the membrane in a sterile filter to provide a predetermined amount of the sterile substitution solution for addition to the extracorporeal circuit.

26 Claims, 3 Drawing Sheets

U.S. PATENT DOCUMENTS

| | | | |
|---|---|---|---|
| 5,702,597 | * 12/1997 | Chevallet et al. | 210/195.2 |
| 5,711,883 | * 1/1998 | Folden et al. | 210/646 |
| 5,808,181 | * 9/1998 | Wamsiedler et al. | 73/38 |
| 5,846,419 | * 12/1998 | Nederlof | 210/323.1 |
| 6,139,748 | * 10/2000 | Ericson et al. | 210/646 |

FOREIGN PATENT DOCUMENTS

| | | |
|---|---|---|
| 0 189 561 B1 | 7/1990 | (EP) . |
| 0 270 794 B1 | 6/1992 | (EP) . |
| 0 278 100 B1 | 7/1992 | (EP) . |
| 0 407 737 B1 | 8/1993 | (EP) . |
| 0 692 268 A1 | 1/1996 | (EP) . |
| 0 692 269 A2 | 1/1996 | (EP) . |
| 0 694 312 A2 | 1/1996 | (EP) . |
| 95/22743 | 8/1995 | (WO) . |

* cited by examiner

DEVICE AND METHOD FOR PREPARATION OF SUBSTITUTION SOLUTION

FIELD OF THE INVENTION

The present invention relates to a method and apparatus for producing a substitution fluid for use during hemodiafiltration or hemofiltration in a hemodialysis machine or for use as filling and rinsing fluid during preparation of a hemodialysis machine.

BACKGROUND OF THE INVENTION

A hemodialysis treatment is used for treating patients who have acute or chronic renal insufficiency. Blood is taken from the patient in an extracorporeal blood circuit and passes through a dialyser which removes uremic toxins in the blood and reconstitutes the blood by balancing electrolytes, such as sodium, potassium, calcium and magnesium, and adding necessary substances, such as bicarbonate. Moreover, a certain amount of fluid is removed from the blood, called ultrafiltrate, since the patient cannot expel superfluous fluids in the normal manner. Hemodialysis primarily uses diffusion through a semipermeable membrane in order to perform this treatment.

Another treatment procedure which has been used more often recently is hemofiltration, whereby the blood is filtered in a hemofilter and the filtrate is discarded. Substitution fluid is then added, either before or after the filtration, for replacing the discarded ultrafiltration fluid. Hemofiltration primarily uses convection for removing the uremic toxins, and the substitution fluid comprises the necessary electrolytes for balancing and fluid addition purpose. A smaller amount of substitution fluid is added compared to the amount of ultrafiltrate fluid which is removed, in order to remove the necessary amount of fluid from the patient.

Another treatment procedure utilized is a combination of hemodialysis and hemofiltration, and is called hemodiafiltration. This procedure is essentially a combination of these two treatment procedures, and uses a hemodiafilter.

These treatment methods are described in numerous text books and it is not necessary to describe them in more detail in the present specification. One description is in the chapter: "Hemodialysis Machines and Monitors" by Polaschegg H D, Levin N W in "Replacement of renal function by dialysis", by Jacobs C, Kjellstrand C M, Koch K M, Winchester J F, 4th ed. Kluwer academic publishers, 1996:333–79.

The above-mentioned substitution fluid can be prepared as a pharmaceutical solution. However, doing so is expensive. Therefore, it is preferred to produce the substitution solution on-line in connection with the dialysis machine, by filtration of the dialysis fluid. However, a preparation method must be devised and adapted for preparing a substitution fluid that is sterile and can be used for infusion purpose.

Thus, a dialysis machine which is adapted for hemofiltration and hemodiafiltration also includes a device for preparing the substitution fluid on-line. This device usually comprises two filters for producing the substitution fluid and for securing the sterility of the prepared fluid.

Some patent specifications describing devices of interest for accomplishing these goals are U.S. Pat. No. 4,209,391, assigned to Cordis Dow; European Patent No. 189,561, assigned to Fresenius; German Patent No. 3,448,262, assigned to Fresenius; U.S. Pat. No. 4,834,888, assigned to Fresenius; European Patent No. 407,737, assigned to Fresenius; German Patent No. 4,240,681, assigned to Fresenius; European Patent No. 692,268, assigned to Fresenius; European Patent No. 165,519, assigned to Gambro; European Patent No. 694,312, assigned to Hospal; and European Patent No. 745,213, assigned to Gambro.

Previous dialysis machines for producing on-line substitution solutions comprise a peristaltic pump arranged upstream of the dialysis machine for propelling the substitution fluid. A peristaltic pump comprises several rollers interacting with a plastic tube pump segment and occluding the pump segment. By moving the roller along the tube while occluding the tube, the fluid is pumped. The substitution fluid flow rate is thus approximately proportional to the rotational speed of the peristaltic pump.

The peristaltic pump is used since it can easily be placed on the front of the machine, and because it cooperates with a tube portion that can be produced as a sterile article. However, the tube portion so utilized has a limited life time. Thus, the pump segment and the second filter must be replaced, for example after one month, which creates comparatively high costs. Also, the peristaltic pump involves added costs, and uses a relatively large additional space on the front of the machine. The peristaltic pump is thus placed on the front since the pump segment must be replaced regularly. All this makes preparation for the treatment complicated.

If the peristaltic pump is used with a disposable tube system and a disposable second filter, the disposable tube system must comprise a pump segment and the second filter. Thus, such a disposable tube system is comparatively expensive and bulky.

The object of the present invention is therefore to provide a method and apparatus which obviates the drawbacks of the prior art dialysis machines.

Another object of the present invention is to provide a dialysis machine for producing substitution fluid on-line, in which the peristaltic pump previously used is dispensed with.

SUMMARY OF THE INVENTION

In accordance with the present invention, these and other objects have now been realized by the invention of apparatus for providing a sterile substitution solution from a dialysis fluid used in connection with the treatment of a patient's blood in an extracorporeal circuit, the apparatus comprising balancing means for comparing a flow of fresh dialysis fluid prior to the treatment of the patient's blood and a flow of spent dialysis fluid after the treatment of the patient's blood, a fresh dialysis circuit for handling the fresh dialysis fluid, a throttle dividing the fresh dialysis circuit into a positive pressure portion and a negative pressure portion, at least one sterile filter including a membrane in the fresh dialysis circuit, the at least one sterile filter being disposed in the positive pressure portion of the fresh dialysis circuit, pressure control means for controlling the pressure in the positive pressure portion in order to pass a predetermined amount of the fresh dialysis fluid through the membrane in the at least one sterile filter in order to provide a predetermined amount of the sterile substitution solution for addition to the extracorporeal circuit. In a preferred embodiment, the apparatus includes a dialyser for treatment of the patient's blood. Preferably, the dialyser is a hemodialysis device, a hemofiltration device or a hemodiafiltration device.

In accordance with one embodiment of the apparatus of the present invention, the fresh dialysis circuit comprises a first conduit disposed between the balancing means and the dialyser, the throttle being disposed in the first conduit, and the apparatus including a second conduit connected to the first circuit at a predetermined location between the balancing means and the throttle, the at least one sterile filter being disposed in the second conduit, and the second conduit being connected to the extracorporeal circuit. In a preferred embodiment, the dialyser is a hemodialysis device, a hemofiltration device or a hemodiafiltration device.

In accordance with a preferred embodiment of the apparatus of the present invention, the apparatus includes a flow meter associated with the first conduit between the predetermined location and the dialyser for measuring the flow of the fresh dialysis fluid to the dialyser, whereby the throttle can be controlled by measurement of the flow by the flow meter and a predetermined flow of the sterile substitution solution can be obtained in the second conduit, the predetermined flow comprising the difference between the flow of the fresh dialysis fluid obtained by the balancing means and the flow of the fresh dialysis fluid through the throttle. Preferably, the throttle comprises an adjustable throttle valve, and adjustable three-way valve, a constant pressure valve, or a constant flow valve.

In accordance with one embodiment of the apparatus of the present invention, the balancing means comprises a first adjustable constant flow pump for delivering a predetermined flow of the fresh dialysis fluid to the first conduit and the throttle comprises a second adjustable constant flow pump for delivering a predetermined flow of the fresh dialysis fluid to the dialyser, whereby a predetermined flow of the sterile substitution solution can be obtained in the second conduit, the predetermined flow of the sterile substitution solution comprising the difference between the predetermined flow of the fresh dialysis fluid in the first conduit and the predetermined flow of the fresh dialysis fluid to the dialyser.

In accordance with another embodiment of the apparatus of the present invention, the at least one sterile filter comprises a first sterile filter and including a second sterile filter associated with the first conduit between the balancing means and the predetermined location.

In accordance with another embodiment of the apparatus of the present invention, the apparatus includes testing means associated with the first conduit for testing the integrity of the at least one sterile filter. Preferably, the testing means comprises an air pump for forcing air into the first conduit. In a preferred embodiment, the at least one sterile filter comprises a first sterile filter and including a second sterile filter associated with the first conduit between the balancing means and the predetermined location. Preferably, the air pump forces the air into the first conduit between the first and second sterile filters, and the apparatus includes a valve located downstream of the second sterile filter. Preferably, the apparatus includes a bypass connector, whereby the valve is disposed downstream of the dialyser and upstream of the bypass connector. In a preferred embodiment, the valve comprises an adjustable throttle valve.

In accordance with another embodiment of the apparatus of the present invention, the apparatus includes testing means associated with the first conduit for testing the integrity of the at least one sterile filter. In a preferred embodiment, the testing means comprises bleed means whereby the first conduit between the first and second sterile filters can be provided with air. Preferably, the apparatus includes a hydrophobic sterile filter disposed between the air pump and the first conduit at a location between the first and second sterile filters.

In accordance with the present invention, a method has also been devised for testing sterile filters in an apparatus according to that described above including producing a positive pressure in the first conduit by means of the air pump, terminating operation of the air pump upon obtaining a predetermined pressure in the first conduit, and measuring the pressure curve in the first conduit by means of a manometer, whereby the condition of the sterile filter may be tested.

In accordance with another embodiment of the method of the present invention for testing sterile filters in the above apparatus, the method includes producing a negative pressure downstream of the dialyser by means of a pump such as an ultrafiltration pump or a dialysate circulation pump, terminating operation of the pump upon obtaining a predetermined pressure downstream of the dialyser, and measuring the pressure curve in the first conduit by means of a dialysate pressure sensor, whereby the condition of the sterile filter may be tested.

In accordance with the present invention, a method has also been provided for providing a sterile substitution solution from a dialysis fluid used in connection with the treatment of a patient's blood in an extracorporeal circuit comprising providing a fresh dialysis fluid, pumping the fresh dialysis fluid through a first conduit to a dialyser by means of a pump, providing an increased pressure in the first conduit by providing a throttle in the first conduit between the pump and the dialyser, obtaining the sterile substitution solution in a sterile filter connected to the first conduit between the pump and the throttle, passing the sterile substitution solution to the extracorporeal circuit, sensing the flow of the dialysis fluid in the first conduit between the connection to the sterile filter and the dialyser, and controlling the throttle based on the sensed flow whereby the flow rate of the sterile substitution solution obtained in the sterile filter can be maintained. In a preferred embodiment, the method includes measuring the flow of the dialysis fluid to the dialyser in the first conduit by means of a flow meter between the connection to the sterile filter and the dialyser, and adjusting the throttle to obtain the flow of the sterile substitution solution as the difference between the flow of the dialyser fluid obtained by the pump and the flow of the dialyser fluid through the throttle.

According to the present invention, such a method and apparatus involves the fact that the second filter is arranged in a portion of the dialysis fluid circuit which is always under a positive pressure. By means of this positive pressure, filtration of the substitution solution takes place without the use of an additional pump.

Apparatus which includes a device for obtaining a positive pressure is disclosed, for example, in U.S. Pat. No. 4,209,391. Moreover, such a previously known dialysis machine is known as the AK-100 Ultra sold by GAMBRO AB.

BRIEF DESCRIPTION OF THE DRAWINGS

Further objects, advantages and features of the present invention will be seen from the following detailed description of several embodiments of the present invention, with reference to the appended drawings in which.

DETAILED DESCRIPTION

Figure 1:
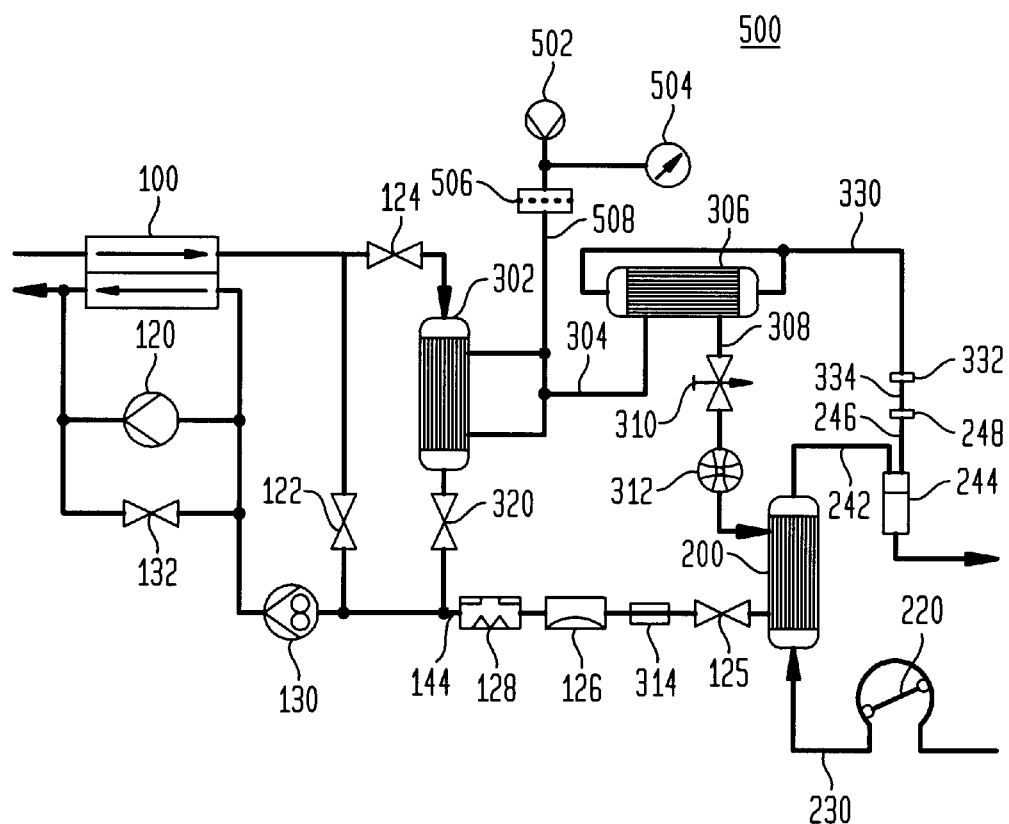
FIG. 1 is a schematic diagram of a first embodiment of the present invention.

Turning to the Figures, in which like reference numerals refer to like elements thereof, FIG. 1 discloses a first embodiment of the present invention, comprising a balancing system 100 for a dialysis fluid.

The term balancing system is intended to refer to a system that works with balancing chambers or balancing pistons, such as for example in the machines series 2008 or 4008 by the Fresenius, the Centry 3 machine of company Cobe, the System 1000 machine of Althin Medical, the MIROCLAV machine of Baxter Deutschland or the DIALOG machine of B. Braun-Melsungen. This term also comprises a balancing system that works with flow meters, such as for example the Integra machine of Hospal. These balancing systems ensure that the amounts of flow at the inlet and outlet are equal, and that is why they often are called "a flow equalizer" in the U.S. patent literature. In these balancing systems, fluid is removed from the patient by a parallel connected ultrafiltration pump 120.

However, the present invention can also be used with a balancing system that produces a predetermined inlet and outlet flow rate differential without additional ultrafiltration pumps, such as for example the AK100 machine of Gambro, see for example European Patent No. 278,100. The inlet flow to the dialyser is slightly smaller than the outlet flow from the dialyser, and the difference corresponds to the amount of ultrafiltration.

The fresh dialysis fluid from the balancing system 100 passes through a concentration and temperature monitor (not shown) and also through a dialysis valve 124 to a first sterile filter 302 comprising a semipermeable membrane. The dialysis valve together with the concentration and temperature monitor and the bypass valve 122 act as a security system and prevents dialysis with an improper dialysis fluid composition and/or temperature. These devices belong to the state of the art.

For rinsing or flushing the sterile filter, the dialysis fluid can flow along the membrane of the filter, and then through a valve 320 to the outlet.

When the valve 320 is closed, the dialysis fluid passes through the membrane of the sterile filter 302 to a line 304 for producing a clean dialysis fluid. From line 304, the dialysis fluid reaches a second sterile filter 306 and passes along the membrane to an outlet line 308, without being filtered. Line 308 is normally connected to a dialyser 200, which also can be a hemofilter or a hemodiafilter as mentioned above.

Line 308 includes a throttle device or throttle valve 310 between the second filter and the dialyser. Moreover, line 308 includes a flow sensor 312.

The dialysis fluid also passes through the membrane of the second sterile filter 306 to produce a sterile substitution fluid in line 330 to be supplied to the blood in an extracorporeal circuit to be described below. Thus, the flow from the first filter 302 is measured or controlled by the balancing unit 100 and then divided into a first flow to the dialyser through throttle valve 310 and flow sensor 312 and a second substitution fluid flow through line 330, and to the blood of the patient. It is desired to control the flow of substitution fluid to obtain the goals of the treatment. By measuring the total flow and the flow to the dialyser, the substitution flow must always be the difference between these flows. A control unit (not shown) adjusts the throttle device so that the desired substitution fluid flow is obtained.

The throttle valve 310 can be a constant pressure valve, which guaranties a constant upstream pressure independent of the flow passing therethrough. The substitution flow is thereby provided by the pressure difference relative to the extracorporeal circuit and the filtration resistance of the sterile filter 306.

Alternatively, the throttle valve 310 can be a constant flow valve, which is adjusted to a certain fluid flow rate which is equal to the flow through the balancing system minus the intended substitution flow. By means of such a valve, there is automatically obtained a pressure which results in the desired substitution fluid flow.

In another alternative, the throttle valve can be an adjustable throttle valve, which is controlled by a control device. The flow meter 312 is arranged downstream of the throttle device 310 but can alternatively be arranged upstream of the throttle device but downstream of the second sterile filter 306. This flow meter reads the difference between the dialysate flowing through the balancing unit 100 and the substitution fluid. Since the flow passing through the balancing unit is either predetermined or measured, the substitution fluid flow can be indirectly measured by the flow meter 312. By means of this information, the throttle device 310 can be adjusted, either manually or by means of a control unit (not shown), so that the desired substitution fluid flow is obtained.

Moreover, the throttle device can be a three-way valve which is adjusted so that the desired proportion of flows are obtained.

The spent dialysis fluid, called the dialysate, leaves the dialyser 200 through a line 144, comprising a second dialyser valve 125 as well as a bypass connector (male or female) 314. Moreover, line 144 comprises a dialysate pressure sensor 126 and a blood leak detector 128. The spent dialysate passes through the balancing system by means of a dialysate circulation pump 130, and then passes to the drain.

Parallel to the balancing system 100 there is another valve 132, which makes possible the separation of air, since many balancing systems are disturbed by air. This valve is controlled by an air detection system (not shown).

The dialysis fluid in the second filter 306 has a positive pressure relative to the atmosphere and to the extracorporeal circuit, and is filtered through the membrane of the filter. By means of line 330 the filtered and sterile substitution fluid reaches a drip chamber connector 248. Line 330 terminates in a male connector 332 attached to an anticontamination intermediate portion 334, which through a line 246 is connected to venous drip chamber 244 of the extracorporeal circuit.

As is known, the extracorporeal circuit comprises a blood pump 220, an arterial tube system 230, the blood portion of the dialyser 200 and a venous tube system 242 incorporating the venous drip chamber 244. The embodiment shown in FIG. 1 is a "post-dilution" device, i.e. the substitution fluid is introduced downstream of the dialyser and the blood is diluted downstream of the dialyser. Alternatively, the substitution fluid can be introduced before the dialyser (pre-dilution), between two dialysers (mid-dilution), before and after, respectively before-between-after the dialysers. The substitution solution can also be introduced before the blood pump in the negative pressure area. The advantage of such a method is that a larger pressure gradient is available for the filtration in sterile filter 306, and the arterial tube system is driven with a higher flow and diluted blood, which decreases the viscosity. See German Patent No. 4,240,681 filed on Aug. 8, 1994.

Figure 5:
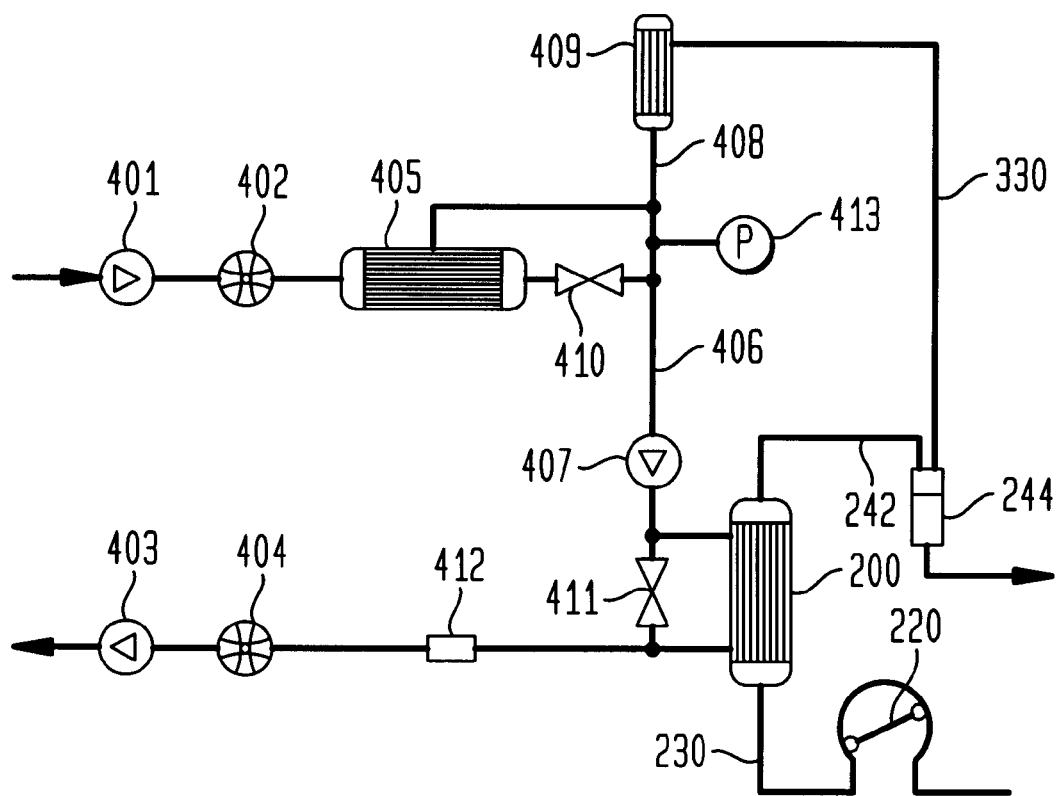
FIG. 5 is a schematic diagram of a fourth embodiment of the present invention.

FIG. 5 discloses a slightly modified embodiment of the present invention. Instead of the balancing system 100, this embodiment utilizes two adjustable constant flow pumps, 401 and 403, and two flow meters, 402 and 404. The first constant flow pump 401 passes about 500 ml/min of dialysis fluid. The second constant flow pump 403 passes about 520 ml/min, and the difference therebetween accounts for the ultrafiltration and is controlled by the computer of the dialysis machine. The flow meters, 402 and 404, are used for measuring the ultrafiltration by calculating the differential flow rate, i.e. 20 ml/min with the above-mentioned figures. It is clear that the above-mentioned figures of flow rates are only exemplary and that other values can be used. Generally, the dialysis flow rate is from about 300 to 700 ml/min, and the ultrafiltration is about 1000 to 4000 ml per treatment. Each treatment usually lasts for about 3 to 5 hours, and is carried out about three times per week.

From the first constant flow meter 401, the dialysis fluid passes a clean dialysate filter 405 and enters a line 406 leading to the dialyser 200. Line 406 further comprises a branch line 408 leading to a sterile filter 409, the outlet of which is connected to the substitution line 330 according to the previous embodiments. From the dialyser 200, the dialysate passes through different devices disclosed as a box 412, such as a blood leak detector, and further to flow meter 404 and constant flow pump 403, and finally to the drain.

Line 408, sterile filter 409 and line 330 are made as a disposable unit integral with the remaining extracorporeal circuit, such as drip chamber 244, line 242, line 230 and pump segment 220. By means of the present invention, this disposable unit can be made without any pump segments, which decreases the costs and complexity significantly. The disposable unit is sterilized during the manufacturing process. Since sterile filter 409 is used only once, it can be made much smaller as is indicated in FIG. 5.

Line 406 comprises a third constant flow pump 407 which is adjusted, for example, to a flow of 350 ml/min, which is the difference between the dialysis flow (500 ml/min) and the desired substitution flow (150 ml/min). The constant flow pumps operate to provide the pressures which are necessary in order to obtain the adjusted flow rates. Thus, the pressure inside the dialyser is adjusted to a negative pressure compared to the blood pressure inside the dialyser so as to provide a desired ultrafiltration. Moreover, the pressure in the branch line 408 is a positive pressure which is necessary for passing the desired amount of substitution fluid through the membrane of filter 409. A pressure sensor 413 is arranged at the branch connection to monitor the pressure before the sterile filter 409. If the pressure is outside a predetermined pressure value, an alarm signal is generated, indicating, for example, a blocked sterile filter, as described in Swedish Patent Application No. 9703403-7 filed Sep. 22, 1997, on behalf of Gambro AB.

For rinsing filter 405, there is provided a valve 410 between a second outlet of the filter and line 406. If the valve 410 is opened and the dialyser is bypassed by a bypass valve 411, the dialysis fluid passes through the filter in parallel with the membrane in order to rinse away possible contaminations on the surface of the membrane.

FIG. 5 discloses a dialysis machine which is adapted for hemodiafiltration in which purification of the blood takes place both by dialysis (diffusion) and by filtration (convection). It is possible to adapt the machine to hemofiltration by opening valve 411 and closing a valve positioned in the line from the constant flow pump 407 to the upper connection to the dialyser in FIG. 5. The dialyser 200 is replaced by a hemofilter having only the lower connection to the dialysis fluid circuit shown in FIG. 5. The constant flow pumps, 401, 403 and 417, will adjust the different flows to obtain the desired conditions for hemofiltration. One possibility is to utilize the following flows: pump 401: 500 ml/min; pump 403: 515 ml/min; and pump 417: 300 ml/min, resulting in a substitution flow of 200 ml/min. Another possibility is to utilize the following flows: pump 401: 200 ml/min; pump 403: 215 ml/min; and pump 417: 0 ml/min, resulting in a substitution flow of 200 ml/min. In the last case, the pump 417 can be replaced by a valve or throttle, being closed. A skilled person can readily realize further such modifications.

The sterile filters, 302 and 306, and dialyser 200, can be controlled for the integrity of the membrane by means of a pressure retention test in a test system 500. Such a test method is described, for example, in European Patent No. 407,737.

A test of the sterile filter will be described with reference to FIG. 2.

Figure 2:
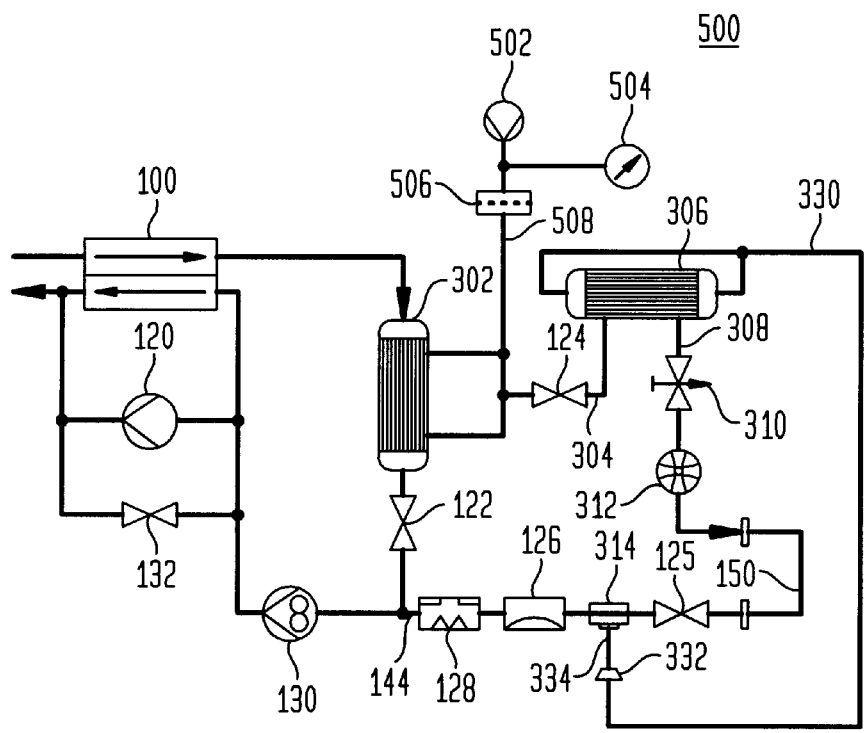
FIG. 2 is a schematic diagram of a second embodiment of the present invention.

FIG. 2 discloses a second embodiment which is modified in relation to FIG. 1, such as described in German Patent No. 3,641,843 (corresponding to U.S. Pat. No. 4,834,888). The dialyser valve is placed between the first sterile filter 302 and the second sterile filter 306. The dialysis fluid line 308 and dialysate fluid line 144 are interconnected by a short-circuit portion 150. The substitution fluid line 330 with the anti-contamination portion 334 is connected to the dialysate line 144 downstream of the second dialyser valve 125 through the bypass connector 314.

For testing the integrity of the membranes of the sterile filers, the bypass valve 122, the first dialyser valve 124 and the bleeding valve 132 are opened, and the second dialyser valve 125 is closed. Pump 502 urges air into the line 304 between the first sterile filter 302 and the second sterile filter 306. In this manner, the dialysis fluid is pressed away, at one side through valve 122 and at the other side through line 330, and it reaches the dialysate line 144 and then by means of pump 130 and valve 132, to the drain. With intact sterile filter membranes, this operation terminates when all fluid has been removed from line 304 between the sterile filters and the interior of the filters up to the membranes, since air can only pass the hydrophile membranes of these filters by diffusion.

Then, the air pressure in line 508 increases, which is registered by a manometer 504. Pump 502 is driven until a positive air pressure, of typically of about 1 bar (1000 hPa) has been built up. The pump is then stopped, and the pressure relaxation curve is followed at the manometer 504. With intact sterile filter membranes, the pressure decreases slowly. If there is a leakage, the pressure decreases faster. The rate of decrease of pressure at which a membrane can be considered tight is dependent on the membrane and is predefined in a control and monitoring unit (not shown).

Figure 3:
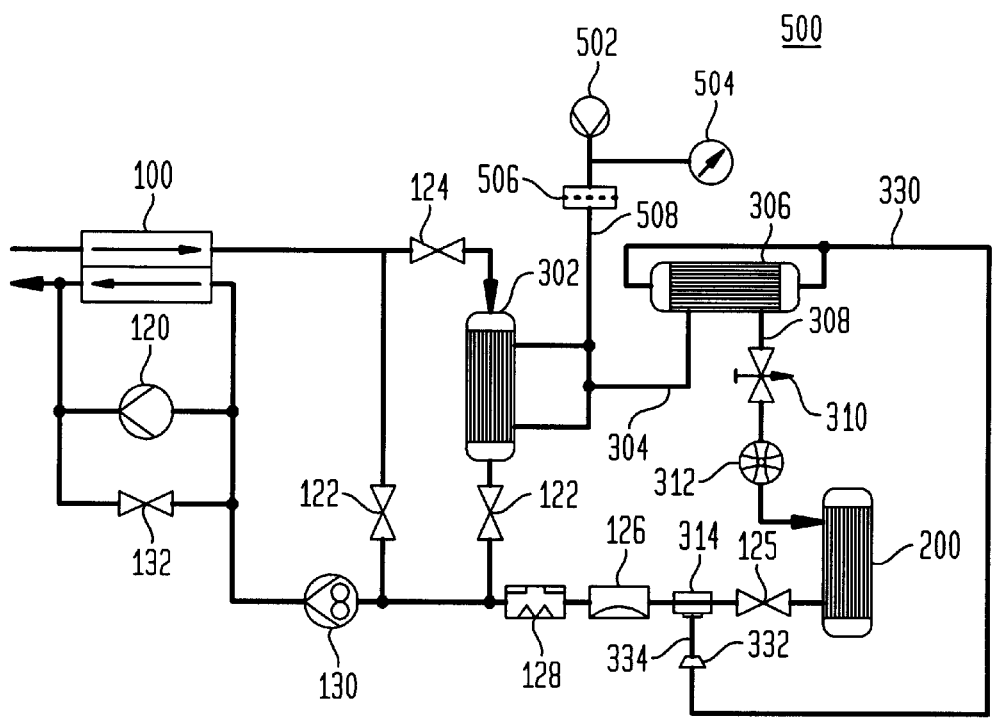
FIG. 3 is a schematic diagram of the first embodiment of the present invention shown in FIG. 1, but adapted for testing the integrity of the filter membranes.
Figure 4:
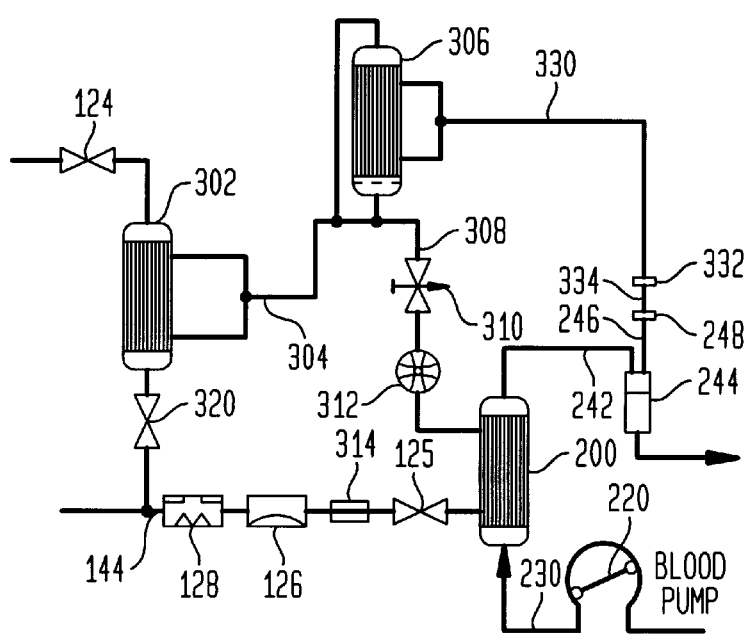
FIG. 4 is a schematic diagram of a third embodiment of the present invention.

It is also possible to test the integrity of the dialyser membranes at the same time, if the dialyser lines, 308 and 144, are connected to the dialyser 200 instead of the short-circuit portion 150 as shown in FIG. 3. The testing of the dialyser is however also possible in a device corresponding to FIG. 2. For testing the sterile filters in a device according to FIG. 1 or 3, the rinse valve 320 is opened and the second dialyser valve 125 is closed. Valves 122 and 124 can be positioned in an arbitrary position. Pump 502 is started, and the testing process takes place as described above.

The dialyser valve 125 can be omitted from the testing process if the throttle device can be completely closed. In this case, the throttle device is closed for the testing process. The simultaneous testing of the dialyser is thus no longer possible. In this case, it is possible to arrange the bypass connector 314 in the area of the short circuit portion 150.

The device can be further modified. What is essential is that the area between the two filters during the test process is connected to the drain only through the membranes of the two filters. In addition, the pump 502 and the manometer 504 are not completely necessary. The test process can also take place with a negative pressure on the dialysate side. In that case, only the hydrophobic sterile filter 506 is necessary, which is open to the atmosphere. For testing purposes, the valves are operated as described and by means of pump 120 or pump 130 plus an opened bleeding valve 132, a negative pressure is generated. The fluid is then pumped out of the area between the two sterile filters, while at the same time air enters through the hydrophobic filter 506. When all fluids have left the area between the two sterile filters, the pressure in the area of the dialysate line 144 decreases, which can be sensed by the dialysate pressure sensor 126. Upon reaching a predetermined negative pressure, the pump 120 is stopped, the valve 132 is closed, and the pressure increase can be determined in a known manner for detecting leakages.

By means of the test process thus described, both sterile filters, and possibly also the dialyser, are tested for leakages. With the device according to FIG. 2, a separate test of the two filters can also be performed. The first sterile filter 302 is tested if valve 124 is closed and valve 122 is opened. The second sterile filter is separately tested if valve 122 is closed and valve 124 is opened. It is then presumed that the balancing unit 100 does not permit any return flow.

The hydrophobic filter 506 is preferably adapted close to the connection 304 for making line 508 as short as possible. It is preferable if line 508 is removed and filter 506 is passed through tangentially. In each case, it is preferable that the test be performed before and after the disinfection operation. Then, the disinfection agent can reach the line 508 and then be removed again.

The sterile filters are disinfected together with the rest of the dialysis machine. It is then necessary that disinfection agents and temperatures are used, which are compatible with the filter material. Thus, filters with membranes of polysulphone and polyvinylpyrolidone cannot be used together with an disinfection agent comprising sodium hypochlorite. For disinfection, the terminal of the substitution fluid line 332, including the anticontamination portion 334, is connected to the bypass connector 314. During disinfection, a positive pressure is maintained in the area of the sterile filters by the throttle device 310, whereby a portion of the disinfection agent circulating in the fluid circuit passes through the filters.

Before start of the next treatment, the disinfection agent is rinsed off in the usual manner. The substitution fluid line is disconnected from bypass connector 314 and connected to a new sterile intermediate portion 334 and to the venous drip chamber 244. The old intermediate portion 334 is discarded. The objective of the anticontamination intermediate portion is to obviate a cross contamination during contact with the patient blood. Usually, the connection portion during the disinfection process is only sterilized at the inner surfaces. A contamination can, however, also take place by means of the outer surfaces, at the generally used Luer connectors. As the intermediate portion is preferably used a non-return valve which is cheaply available from, for example, the infusion technique. This non-return valve can be provided with one or two additional tube portions. Also, the complete tube portion 330 can be made as a disposable article and the separate intermediate portion 334 is then unnecessary. This is specially advantageous if the second sterile filter 306 has only one connector at the filter side.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. Apparatus for providing a sterile substitution solution from a dialysis fluid used in connection with the treatment of a patient's blood, said apparatus comprising an extracorporeal circuit for handling said patient's blood, said extracorporeal circuit including blood treatment apparatus for treating said patient's blood with fresh dialysis fluid and for providing a spent dialysis fluid therefrom, balancing means for comparing a flow of said fresh dialysis fluid prior to said treatment of said patient's blood and flow of said spent dialysis fluid after said treatment of said patient's blood, a fresh dialysis circuit for handling said fresh dialysis fluid prior to said blood treatment apparatus, a throttle dividing said fresh dialysis circuit into a positive pressure portion and a negative pressure portion, at least one sterile filter including a membrane in said fresh dialysis circuit, whereby said at least one sterile filter is not in contact with said patient's blood, said at least one sterile filter being disposed in said positive pressure portion of said fresh dialysis circuit, and pressure control means for controlling the pressure in said positive pressure portion in order to pass a predetermined amount of said fresh dialysis fluid through said membrane in said at least one sterile filter in order to provide a predetermined amount of said sterile substitution solution for addition to said extracorporeal circuit.

2. The apparatus of claim 1 wherein said blood treatment apparatus comprises a dialyser.

3. The apparatus of claim 2 wherein said dialyser is selected from the group consisting of a hemodialysis device, a hemofiltration device and a hemodiafiltration device.

4. The apparatus of claim 2 wherein said fresh dialysis circuit comprises a first conduit disposed between said balancing means and said dialyser, said throttle being disposed in said first conduit, said apparatus including a second conduit connected to said first conduit at a predetermined location between said balancing means and said throttle, said at least one sterile filter being disposed in said second conduit, and said second conduit being connected to said extracorporeal circuit.

5. The apparatus of claim 4 wherein said dialyser is selected from the group consisting of a hemodialysis device, a hemofiltration device and a hemodiafiltration device.

6. The apparatus of claim 4 wherein said pressure control means comprises a flow meter associated with said first conduit between said predetermined location and said dialyser for measuring the flow of said fresh dialysis fluid to said dialyser, and throttle control means for controlling said throttle based on measurement of said flow by said flow meter and a predetermined flow of said sterile substitution solution can be obtained in said second conduit, said predetermined flow comprising the difference between said flow of said fresh dialysis fluid obtained by said balancing means and said flow of said fresh dialysis fluid through said throttle.

7. The apparatus of claim 4 wherein said balancing means comprises a first adjustable constant flow pump for delivering a predetermined flow of said fresh dialysis fluid to said first conduit and said throttle comprises a second adjustable constant flow pump for delivering a predetermined flow of said fresh dialysis fluid to said dialyser, whereby a predetermined flow of said sterile substitution solution can be obtained in said second conduit, said predetermined flow of said sterile substitution solution comprising the difference between said predetermined flow of said fresh dialysis fluid in said first conduit and said predetermined flow of said fresh dialysis fluid to said dialyser.

8. The apparatus of claim 4 wherein said at least one sterile filter comprises a first sterile filter and including a second sterile filter associated with said first conduit between said balancing means and said predetermined location, whereby said fresh dialysis fluid flows through said second sterile filter in said first conduit before flowing through said first sterile filter in said second conduit.

9. The apparatus of claim 8 including testing means associated with said first conduit for testing the integrity of said at least one sterile filter.

10. The apparatus of claim 1 wherein said throttle comprises an adjustable throttle valve.

11. The apparatus of claim 1 wherein said throttle comprises an adjustable three-way valve.

12. The apparatus of claim 1 wherein said throttle comprises a constant pressure valve.

13. The apparatus of claim 1 wherein said throttle comprises a constant flow valve.

14. The apparatus of claim 1 including testing means associated with said first conduit for testing the integrity of said at least one sterile filter.

15. The apparatus of claim 14 wherein said testing means comprises an air pump for forcing air into said first conduit.

16. The apparatus of claim 15 wherein said blood treatment apparatus comprises a dialyser and said fresh dialysis circuit comprises a first conduit disposed between said balancing means and said dialyser, said throttle being disposed in said first conduit, said apparatus including a second conduit connected to said first conduit at a predetermined location between said balancing means and said throttle, said at least one sterile filter being disposed in said second conduit, and said second conduit being connected to said extracorporeal circuit.

17. The apparatus of claim 15 wherein said at least one sterile filter comprises a first sterile filter and including a second sterile filter associated with said first conduit between said balancing means and said predetermined location, whereby said fresh dialysis fluid flows through said second sterile filter in said first conduit before flowing through said first sterile filter in said second conduit.

18. The apparatus of claim 17 wherein said air pump forces said air into said first conduit between said first and second sterile filters, and including a valve located downstream of said second sterile filter.

19. The apparatus of claim 18 including a bypass connector for connecting said second conduit directly to said first conduit and bypassing said dialyser, wherein said valve is disposed downstream of said dialyser and upstream of said bypass connector.

20. The apparatus of claim 18 wherein said valve comprises an adjustable throttle valve.

21. The apparatus of claim 17 wherein said testing means comprises bleed means whereby said first conduit between said first and second sterile filters can be provided with air.

22. The apparatus of claim 21 including a hydrophobic sterile filter disposed between said air pump and said first conduit at a location between said first and second sterile filters.

23. A method for testing sterile filters in apparatus according to claim 22 including producing a negative pressure downstream of said dialyser by means of a pump selected from the group consisting of an ultrafiltration pump and a dialysate circulation pump, and permitting a negative pressure to be generated in said both said first and second sterile filters, terminating operation of said pump upon obtaining a predetermined pressure downstream of said dialyser, and measuring the pressure curve in said first conduit by means of a dialysate pressure sensor, whereby the condition of said sterile filter may be tested.

24. A method for testing sterile filters in an apparatus according to claim 21 including producing a positive pressure in said first conduit by means of said air pump, and permitting said air to pass through both said first and second sterile filters, terminating operation of said air pump upon obtaining a predetermined pressure in said first conduit, and measuring the pressure curve in said first conduit by means of a manometer, whereby the condition of said sterile filter may be tested.

25. A method for providing a sterile substitution solution from a dialysis fluid used in connection with the treatment of a patient's blood in an extracorporeal circuit comprising providing a fresh dialysis fluid, pumping said fresh dialysis fluid through a first conduit to a dialyser by means of a pump, providing an increased pressure in said first conduit by providing a throttle in said first conduit between said pump and said dialyser, obtaining said sterile substitution solution in a sterile filter connected to said first conduit at a connection between said pump and said throttle, passing said sterile substitution solution to said extracorporeal circuit, sensing the flow of said dialysis fluid in said first conduit between said connection to said sterile filter and said dialyser, and controlling said throttle based on said sensed flow whereby the flow rate of said sterile substitution solution obtained in said sterile filter can be maintained.

26. The method of claim 25 including measuring the flow of said dialysis fluid to said dialyser in said first conduit by means of a flow meter between said connection to said sterile filter and said dialyser, and adjusting said throttle to obtain said flow of said sterile substitution solution as the difference between said flow of said dialyser fluid obtained by said pump and said flow of said dialyser fluid through said throttle.

* * * * *

UNITED STATES PATENT AND TRADEMARK OFFICE
CERTIFICATE OF CORRECTION

PATENT NO. : 6,280,632 B1
DATED : August 28, 2001
INVENTOR(S) : Polaschegg

It is certified that error appears in the above-identified patent and that said Letters Patent is hereby corrected as shown below:

<u>Title page,</u>
Item [75], delete "(AU)" and insert therefor -- (AT) --.

<u>Column 11,</u>
Line 50, delete "15" and insert therefor -- 16 --.

Signed and Sealed this

Sixteenth Day of April, 2002

Attest:

JAMES E. ROGAN
*Attesting Officer*     *Director of the United States Patent and Trademark Office*